US005519635A

United States Patent [19]
Miyake et al.

[11] Patent Number: 5,519,635
[45] Date of Patent: May 21, 1996

[54] APPARATUS FOR CHEMICAL ANALYSIS WITH DETACHABLE ANALYTICAL UNITS

[75] Inventors: Ryo Miyake, Chiyoda; Masaharu Ishii, Ushiku; Hideo Enoki, Chiyoda; Isao Yamazaki, Tsuchiura; Kazumichi Imai, Katsuta; Tadafumi Kuroishi, Naka; Yu-ming Hsueh, Katsuta, all of Japan

[73] Assignee: Hitachi Ltd., Japan

[21] Appl. No.: 301,028

[22] Filed: Sep. 6, 1994

[30] Foreign Application Priority Data

Sep. 20, 1993 [JP] Japan .................................. 5-232791

[51] Int. Cl.$^6$ ................................................ G01N 35/10
[52] U.S. Cl. ........................ 364/497; 422/58; 422/67; 422/70; 422/101; 436/177; 436/180; 436/43
[58] Field of Search .................................. 364/496–499; 422/58, 63, 67, 70, 81, 101; 436/43, 174, 175, 177, 180

[56] References Cited

U.S. PATENT DOCUMENTS

| | | |
|---|---|---|
| 3,775,595 | 11/1973 | Posse et al. |
| 3,916,157 | 10/1975 | Roulette et al. ................... 235/449 |
| 4,483,927 | 11/1984 | Takekawa ........................... 364/497 |
| 5,000,923 | 3/1991 | Coville et al. ...................... 422/102 |
| 5,104,621 | 4/1992 | Pfost et al. ......................... 422/63 |
| 5,122,342 | 6/1992 | McCulloch et al. ............... 364/497 |
| 5,266,272 | 11/1993 | Griner et al. ....................... 422/104 |
| 5,270,006 | 12/1993 | Uchigaki et al. ................... 422/63 |
| 5,282,149 | 1/1994 | Grandone et al. .................. 364/497 |
| 5,362,648 | 11/1994 | Koreyasu et al. .................. 436/48 |
| 5,397,539 | 3/1995 | Hayashi et al. .................... 422/65 |
| 5,405,510 | 4/1995 | Betts et al. ......................... 204/153.1 |
| 5,428,470 | 6/1995 | Labriola, II ........................ 364/496 |

FOREIGN PATENT DOCUMENTS 61-42211  8/1986  Japan .

OTHER PUBLICATIONS

A Three–Dimensional Micro Flow System For A Multi–Step Chemical Analysis, Elizabeth Verpoorte, Proc. of the 7th International Conference of Solid–State Sensors and Actuators, pp. 939–943.

*Primary Examiner*—Emanuel T. Voeltz
*Assistant Examiner*—Kyle J. Choi
*Attorney, Agent, or Firm*—Evenson, McKeown, Edwards & Lenahan

[57] ABSTRACT

In order to provide an apparatus for chemical analysis capable of eliminating time consuming changing connections of flow paths and analytical elements, and of operating for analysis without any special knowledge, the apparatus for chemical analysis comprises a main body of analytical apparatus provided with sampling device for sucking sample, liquid controller for transferring the sucked sample and reagents, and detector for measuring the sample, and analytical unit provided with a liquid connector and a signal connector for connecting to the main body of analytical apparatus, and memory storing at least analytical method, and analysis of the sample is performed by attaching and fixing the analytical unit to said main body of analytical apparatus, transferring at least analytical method stored in the memory to the main body of analytical apparatus, and analyzing the sample in accordance the said analytical method.

22 Claims, 11 Drawing Sheets

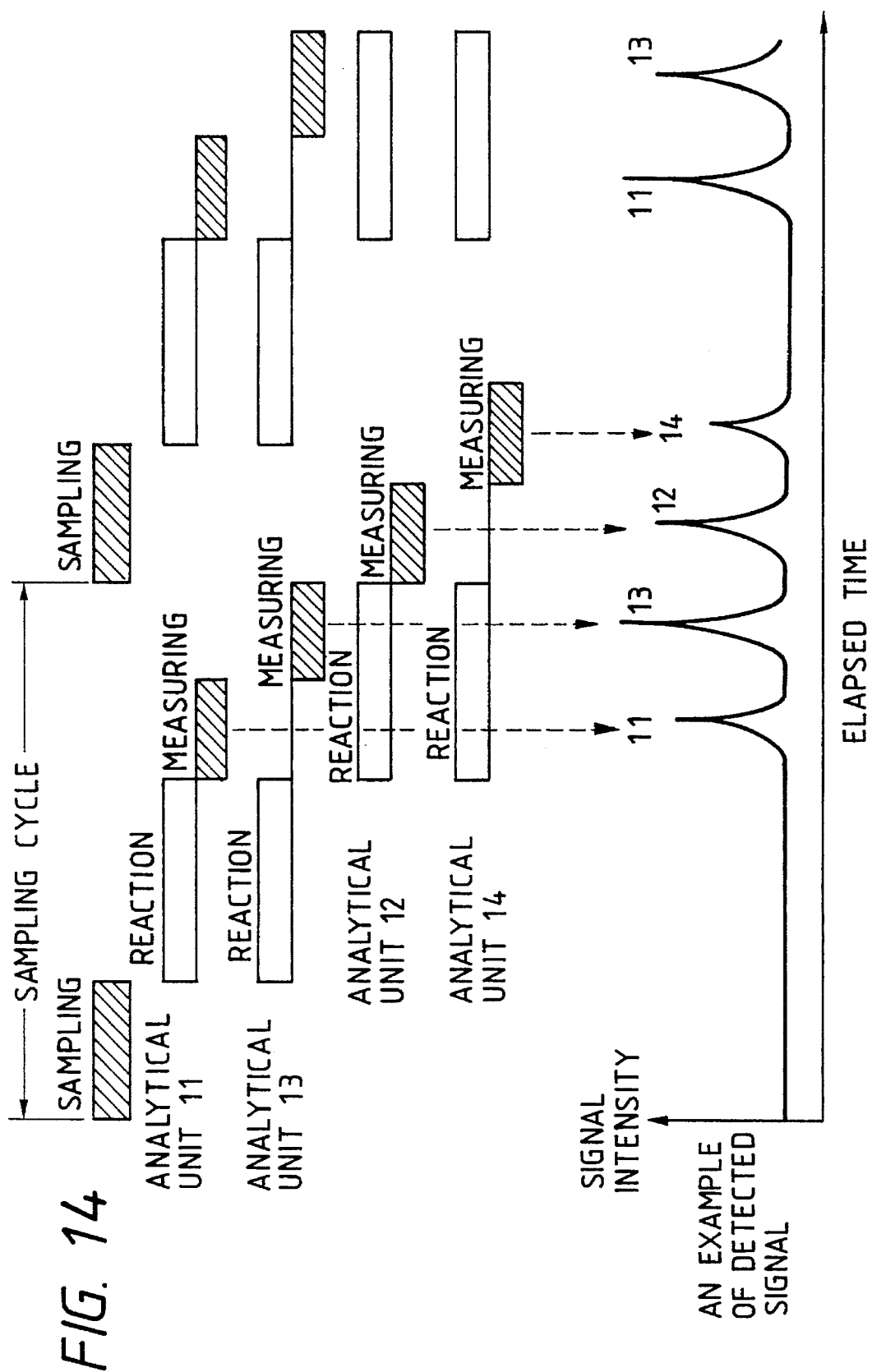

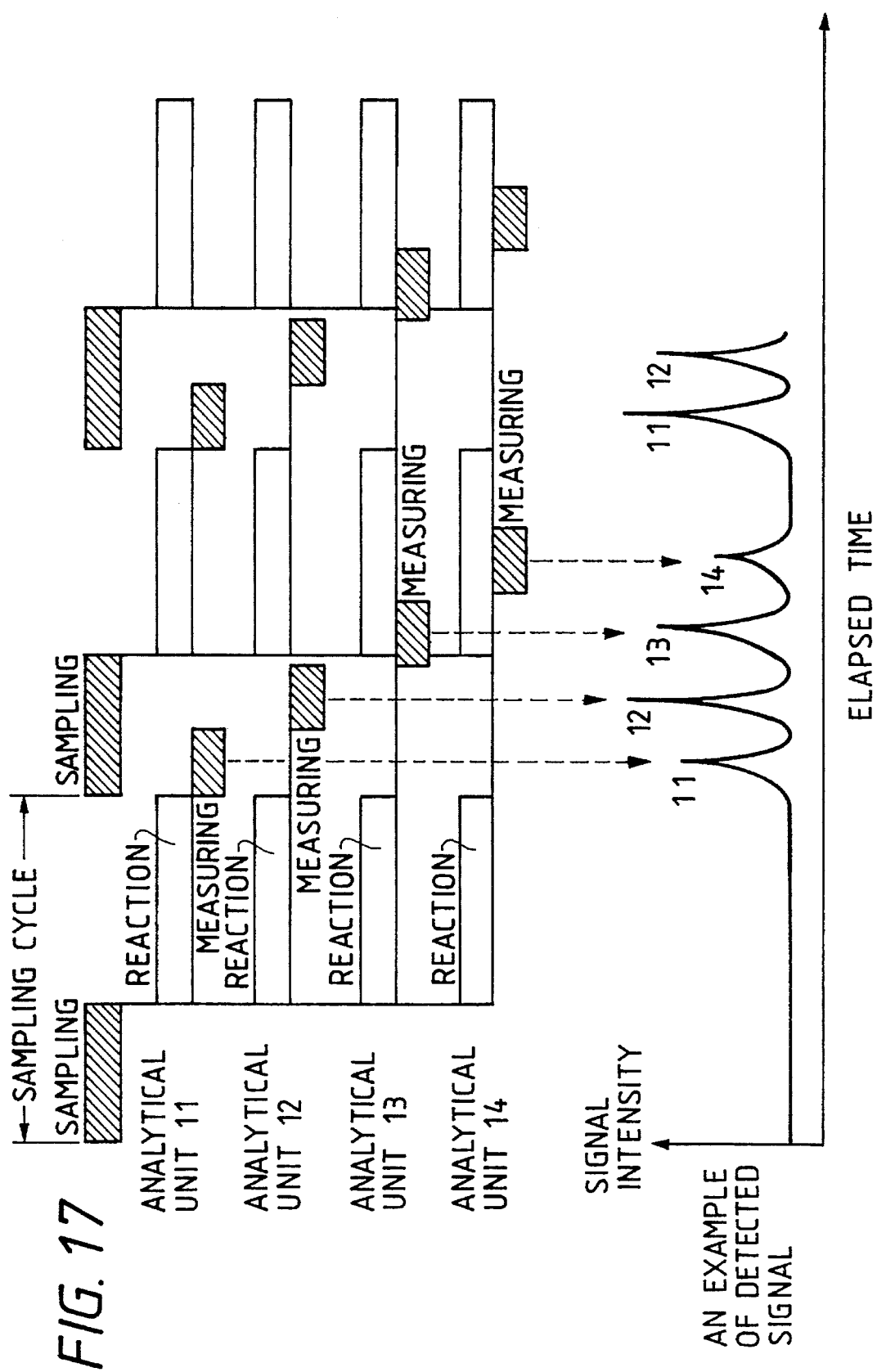

APPARATUS FOR CHEMICAL ANALYSIS WITH DETACHABLE ANALYTICAL UNITS

BACKGROUND OF THE INVENTION

1. Field of the Invention

The present invention relates to apparatus for chemical analysis, especially, for chemical analysis to measure properties, concentration, and others of dissolved constituents in fluid.

2. Prior Art

As for an example of conventional apparatus for chemical analysis, an apparatus for chemical analysis having an analytical path to analyze silver nitrate is known. Operation of the apparatus is explained briefly hereinafter.

First, a sampling valve (a) is activated to supply a sample including $NO_3$ into carrier liquid in a mixing tube (b) in a manner like a sandwich. Next, a pump (c) is activated to flow the sample into the mixing tube (b) for mixing and diluting the sample with the carrier liquid to a designated concentration. A necessary period for flowing the sample to a sampling valve (d) is previously calculated based on velocity of the carrier liquid, and after a predetermined elapsed time, the sampling valve (d) is activated to supply a part of the diluted sample into carrier fluid in another mixing tube (e) for diluting the diluted sample again to a far diluted condition. Next, a reducing column reduces $NO_3$ in the diluted sample to $NO_2$. At an injection portion, a coloration reagent for $NO_2$ is added to the reduced sample and mixed with a mixing tube (g) to react sufficiently, and then, a colorimetric quantitative analysis is performed with light having a designated wave length.

In other examples of analytical apparatus, an analytical apparatus is composed of a path suitable for analyzing silic acid coexisting with phosphoric acid. First, a coloration reagent 1 is added to a sample with carrier liquid, and coloring reactions for both phosphoric acid and silic acid are caused in a successive mixing tube (h). Subsequently, a pump (i) is activated to add a reagent for diminishing the coloration of the phosphoric acid to the sample, after passing through a mixing tube (j), a colorimetric quantitative analysis for silic acid is performed using an absorptiometric flow cell (k).

As for an example of other prior art, a continuous flow analytical method has been disclosed in JP-A-61-42211 (1986). An apparatus for the above method forms reaction paths by combining a several liquid elements which are formed of mixing path blocks having a designated length. When changing an analytical object, the number of the blocks can be varied, other reaction path can be connected to an intermediate portion of the reaction path, and other variation can be applied for forming optimum mixing and reaction paths suitable for the method of above chemical analysis. Operation of the apparatus is the same as the operation of the above described two prior art.

An example of manufacturing the above apparatus for chemical analysis using microprocessing has been disclosed in a reference (Elizabeth Verpoorte et al "A Three-Dimensional Micro Flow System for a Multi-step Chemical Analysis" Proc. of The 7th International Conference of Solid-State Sensors and Actuators). In the above reference, a method for manufacturing small size analytical apparatus for chemical analysis of phosphoric acid concentration by combining two silicon substrates whereon fine mixing paths and a micropump are formed respectively by photolithography is disclosed. Operation of the analytical apparatus is the same as the operation in the above prior art.

As the above two examples reveal, each of chemical analysis for nitric acid and phosphoric acid requires quite different flow paths composition each other. Furthermore, JP-A-61-42211 (1986) disclosed a same example as the above examples. Generally speaking, when an object of chemical analysis differs, composition such as flow paths, columns, and flow cell must be rearranged in accordance with the object. Therefore, apparatus based on prior art requires a large amount of man-hours for changing connection, and hence, it is impossible to analyze many kinds of samples in a short time. Even if the connection changing has been completed, it is necessary further to settle flow conditions such as merging timing of a sample and a reagent, and a flow rate of carrier liquid, and measuring conditions of a detector, and other conditions precisely for each analytical items. Therefore, significantly high grade special knowledge is required.

In data processing after collecting measuring data, the processing methods differ each other significantly depending on kinds of analytical objects. Accordingly, repeated settlements of processing condition corresponding to analytical objects were required, and there has been a defect such as inconvenience.

Recently, demands for chemical analysis apparatus are expanding from a purpose for research in spots to industrial uses such as quality control in medical manufacturers and food industries, and accordingly, an usage wherein a large amount of samples are analyzed fast is becoming major. On the other hand, a measuring objective range of chemical analysis is expanding rapidly as represented by increasing items of water quality analysis. As a result, demands for multipurpose type analytical apparatus which performs various kinds of analysis by only one apparatus have been increased. A trial to overcome the inconvenience of prior art described in the above references by reducing size of the apparatus itself has been continuing, but, an appropriate apparatus which makes it possible to analyze multi-items concurrently has not been proposed yet.

SUMMARY OF THE INVENTION (1) Objects of the Invention:

First object of the present invention is to provide an analytical apparatus capable of being operated and performing analysis without changing connection of flow paths and analytical elements which hitherto required a large amount of man-hours, and also without any special knowledge in order to solve the above described problems.

Second object of the present invention is to provide an analytical apparatus capable of performing various kind of chemical analysis in a short time for a large amount of samples.

(2) Methods of solving the Problems:

In order to realize the above first object of the present invention, an apparatus for chemical analysis is provided by the present invention, which is characterized in comprising a main body of analytical apparatus having sampling means for sucking samples, liquid controlling means for transferring sucked samples and reagents, and detecting means for measuring samples, and an analytical unit having liquid connector, electrical signal connector, both of which are connected to the main body of analytical apparatus, and a memory means storing at least analytical methods, and further is characterized in that the analytical methods stored in the memory means are transferred to the main body of analytical apparatus by connecting the analytical unit to the main body of analytical apparatus, and the samples are analyzed in accordance with the transferred analytical methods.

Further, an apparatus for chemical analysis relating to the present invention is characterized in comprising a main body of analytical apparatus and an analytical unit having memory means for storing analytical process steps and processing method of observed data, wherein the main body of analytical apparatus has sampling means for sucking samples, liquid controlling means for transferring sucked samples and reagents, detecting means for measuring samples, controller for reading out the analytical process steps stored in the memory means in the analytical unit through electrical signal connector in the analytical unit and controlling the sampling means, liquid controlling means and the detecting means, and signal processors for reading out the processing method of observed data stored in the memory means in the analytical unit and processing the observed data, and further is characterized in that the analysis of the samples is performed by connecting the analytical unit to the main body of the analytical apparatus.

Furthermore, an apparatus for chemical analysis relating to the present invention is characterized in comprising a main body of analytical apparatus having sampling means for sucking samples, liquid controlling means for transferring sucked samples and reagents, and detecting means for measuring samples, and an analytical unit having liquid connector, electrical signal connector, both of which are connected to the main body of analytical apparatus, a memory means storing at least analytical methods, and mixing means for the samples and the reagents, wherein the liquid connector has connectors for the samples, reagents, and mixed and reacted samples. And further the apparatus for chemical analysis is characterized in that, by connecting the analytical unit to the main body of the analytical apparatus, the sample and the reagent are transferred to the analytical unit through the liquid connector and mixed together for a reaction, the mixed and reacted sample is transferred to the detecting means in the main body of analytical apparatus, and the sample is analyzed in accordance with the analytical method stored in the memory means.

Further, an apparatus for chemical analysis relating to the present invention is characterized in comprising a main body of analytical apparatus having sampling means for sucking samples, liquid controlling means for transferring sucked samples and reagents, and detecting means for measuring samples, and an analytical unit having liquid connector, electrical signal connector, both of which are connected to the main body of analytical apparatus, a memory means storing analytical processing steps and processing methods for observed data, and mixing means for the samples and the reagents. And further the apparatus for chemical analysis is characterized in that, by connecting the analytical unit to the main body of the analytical apparatus, electric signals, the sample, and the reagent are transferred between the analytical unit and the main body of the analytical apparatus each other, and the sample is analyzed.

An analytical unit having at least one mixing and reacting means, liquid connectors for transferring samples and reagents, flow paths arranged and piped among the fluid connectors in corresponding to methods of chemical analysis suitable for analytical items, memory means for storing processing steps of samples and processing methods of observed data, and signal connectors for transferring stored content in the memory means, relating to the present invention is characterized in that members equipped to a main body of analytical apparatus are controlled in accordance with the processing steps of samples and processing methods of observed data by connecting the analytical unit to the main body of analytical apparatus, and the sample is analyzed.

Further, a separating and purifying means is arranged in the above analytical unit corresponding to analytical methods suitable for the analytical items. And, the analytical unit is provided with a detector for measuring processed samples, and signal connectors for transferring observed data at the detector to the main body of analytical apparatus, and the main body of analytical apparatus is provided with a signal processor for receiving the observed data from the analytical unit through the signal connector and processing the observed data in accordance with the data processing methods suitable for the analytical items. Further, the main body of analytical apparatus is provided with signal connectors for receiving driving signals for controlling operation of the liquid controlling means and the detector from the analytical unit. The analytical unit is provided with mixing and reacting means comprising flow paths for reagents, flow paths for samples, merging portions for the above two flow paths, and flow paths for mixing subsequent to the merging portions. The analytical unit has separating and purifying means which is chromatocolumn.

The analytical unit is provided with a mixing and reacting means comprising a flow path for reagents, a flow path for samples, one of which is provided with a large number of fine nozzles on its wall, and a merging portion which is composed so that one path connects to other path through the above fine nozzles. Further, a whole or a part of the analytical unit is manufactured integrally by precise micro technique.

In order to realize the above second object of the present invention, an apparatus for chemical analysis is provided by the present invention, wherein a plurality of analytical units having memory means for storing processing methods for processing analytical items are provided corresponding to various analytical items, and a main body of the apparatus for chemical analysis is composed so as to be connected with the analytical units, which is characterized in that the main body of analytical apparatus has sampling means for sucking samples, liquid controlling means for transferring sucked samples and reagents, and detecting means for measuring samples, and performs chemical analysis on plural various analytical items on a single sample by reading out processing methods stored in memory means in the analytical unit through electrical signal connectors of the analytical unit and controlling the sampling means, the liquid controlling means, and the detecting means.

The main body of the analytical apparatus, which is composed so that a plurality of analytical units having memory means for storing analytical processing steps on various analyzing items and processing methods for observed data can be connected, is characterized in having sampling means for sucking samples, liquid controlling means for transferring sucked samples and reagents, detecting means for measuring samples, controllers for reading out analytical processing steps stored in memory means in the analytical unit through electrical signal connectors of the analytical unit and controlling the sampling means, the liquid controlling means, and the detecting means, and signal processor for reading out processing methods stored in memory means in the analytical unit through electrical signal connectors of the analytical unit and processing observed data, and that chemical analysis is performed by controlling the sampling means, the liquid controlling means, and the detecting means so as not to interfere mutually each analysis of respective analytical unit by connecting respective analytical unit to the main body of analytical apparatus on plural various analytical items on a single sample by reading out processing methods stored in memory means in the analytical unit through electrical signal connectors of the analytical unit and controlling the sampling means, the liquid controlling means, and the detecting means.

Furthermore, an apparatus for chemical analysis is provided by the present invention, wherein a plurality of analytical units are prepared for corresponding to analytical items, flows of samples and reagents in plural analytical units are controlled collectively, and samples processed at respective analytical units are received collectively, the main body of analytical apparatus for determining physical properties of samples has a collective fluid connector and a collective signal connector which collect fluid connectors and signal connectors respectively from each analytical units together to a point, sampling means for sucking samples, liquid controlling means for transferring sucked samples and reagents, detecting means for measuring samples, controllers for collectively reading out contents stored in memory means in collective analytical units and controlling the sampling means, the liquid controlling means, and the detecting means in accordance with the read out contents, signal processor for processing observed data, informing means for displaying and recording the processed result, collective liquid connectors of each analytical units, and collective connecting portions for connecting with collective signal connectors, transferring samples and reagents, and transmitting recorded contents on processing steps of the samples and processing methods of observed data.

The above described main body of the analytical apparatus having connecting portions for connecting a plurality of analytical units is provided with liquid controlling means for controlling liquid flow in respective analytical units through the connecting portions, controllers for reading out contents stored in the memory means of the plural analytical unit and controlling the liquid controlling means and the detecting means through the connecting portions in accordance with the stored contents corresponding to each analytical items, and signal processors for reading out processing methods of observed data stored in the memory means of respective analytical units and processing the observed data through the connecting portions.

Further, the above described main body of the analytical apparatus having memory portions for storing sample processing steps and observed data corresponding to plural analytical items is provided with controllers for reading out contents stored in the memory portions and controlling the liquid controlling means and the detecting means, and signal processors for reading out processing methods of observed data stored in the memory portions and processing the observed data in accordance with the read out contents.

In order to achieve the first object, the apparatus for chemical analysis relating to the present invention is composed as the above described. And as the analytical units are prepared for respective analytical items and analytical elements, flow paths, and others are composed so as to fit the analytical items, time consuming changing connections of the flow paths and analytical elements can be avoided. Further, as detailed flow conditions, analytical methods, data processing methods, and others for analysis are stored in the analytical units, operation of the apparatus and analysis are possible without any specialized knowledge.

Furthermore, the following procedure is adoptable depending on necessity. First, suitable analytical units for intended analytical content are selected and connected to the main body of the analytical apparatus. At the connection, liquid connectors and signal connectors of the analytical units are connected to connecting portion in the main body of the analytical apparatus. Subsequently, controllers and signal processors in the main body of the analytical apparatus start to operate, and signals containing processing steps of samples, analytical methods, data processing methods are transmitted from memory means in the analytical units to the controllers and signal processors through the signal connectors. In accordance with the transmitted processing steps, the following liquid flow is controlled. First, sampling means sucks a designated amount of sample. Next, liquid controlling means transfers the sucked sample from the sampling means to the analytical unit through the liquid connector.

The sample is introduced into separating and purifying portion in the analytical unit, and designated components in the sample are separated respectively. The separated samples are introduced into mixing and reacting means. The liquid controlling means transfers designated reagents from the main body of the analytical apparatus to the mixing and reacting means in the analytical unit separately through respective paths in the liquid connector with designated timings and flow rates. At the mixing and reacting means, the separated samples and designated reagents are mixed and reacted under designated conditions. The reacted samples are returned by the liquid controlling means to the main body of the analytical apparatus again through the liquid connectors, and transferred into detecting means. At the detecting means, the sample is analyzed in accordance with a designated analytical method. The controller and the signal processor read out analytical results from the detecting means, process data on the samples in accordance with a designated data processing method, and transfer results of the data processing to display means. The display means indicates the results of the data processing.

In order to achieve the second object, the apparatus for chemical analysis relating to the present invention is composed as the above described. And, as the collective analytical unit or a plurality of analytical units which are connected to the main body of the analytical apparatus process the samples taken successively at a time or orderly in a short time, complex chemical analysis as previously described in the example of prior art can be performed on a several kinds of samples in a short time.

Furthermore, the following procedure is adoptable depending on necessity. First, a plurality of analytical units suitable for intended analytical content are selected and connected to the main body of the analytical apparatus. At the connection, a collective liquid connector and a collective signal connector, or liquid connectors and signal connectors of the respective analytical units are connected to connecting portion in the main body of the analytical apparatus. Subsequently, controllers and signal processors in the main body of the analytical apparatus start to operate, and signals containing processing steps of samples, analytical methods, data processing methods are transmitted from memory means in the collective analytical units or analytical units to the controllers and signal processors through the signal connectors. In accordance with the transmitted processing steps, the liquid flow is controlled depending on analytical items orderly or at a time. First, sampling means sucks a designated amount of sample. Next, liquid controlling means transfers the sucked sample from the sampling means to the analytical unit through the liquid connector.

The sample is introduced into separating and purifying portion in the analytical unit, and designated components in the sample are separated respectively. The separated samples are introduced into mixing and reacting means. The liquid controlling means transfers designated reagents from the main body of the analytical apparatus to the mixing and reacting means in the analytical unit separately through respective paths in the liquid connector with designated timings and flow rates. At the mixing and reacting means, the separated samples and designated reagents are mixed and reacted under designated conditions. The reacted samples are returned by the liquid controlling means to the main body of the analytical apparatus again through the liquid connectors, and transferred into detecting means. At the detecting means, the sample is analyzed in accordance with a designated analytical method. The controller and the signal processor read out analytical results from the detecting means, process data on the samples in accordance with a designated data processing method, and transfer results of the data processing to display means. The display means indicates the results of the data processing.

BRIEF DESCRIPTION OF THE DRAWINGS

FIG. 14 is an illustration for explaining operation principle of the apparatus for chemical analysis shown in FIG. 11, FIG. 17 is an illustration for explaining operation principle of the apparatus for chemical analysis shown in FIG. 15.

DETAILED DESCRIPTION OF THE PREFERRED EMBODIMENTS

Embodiment 1

Figure 1:
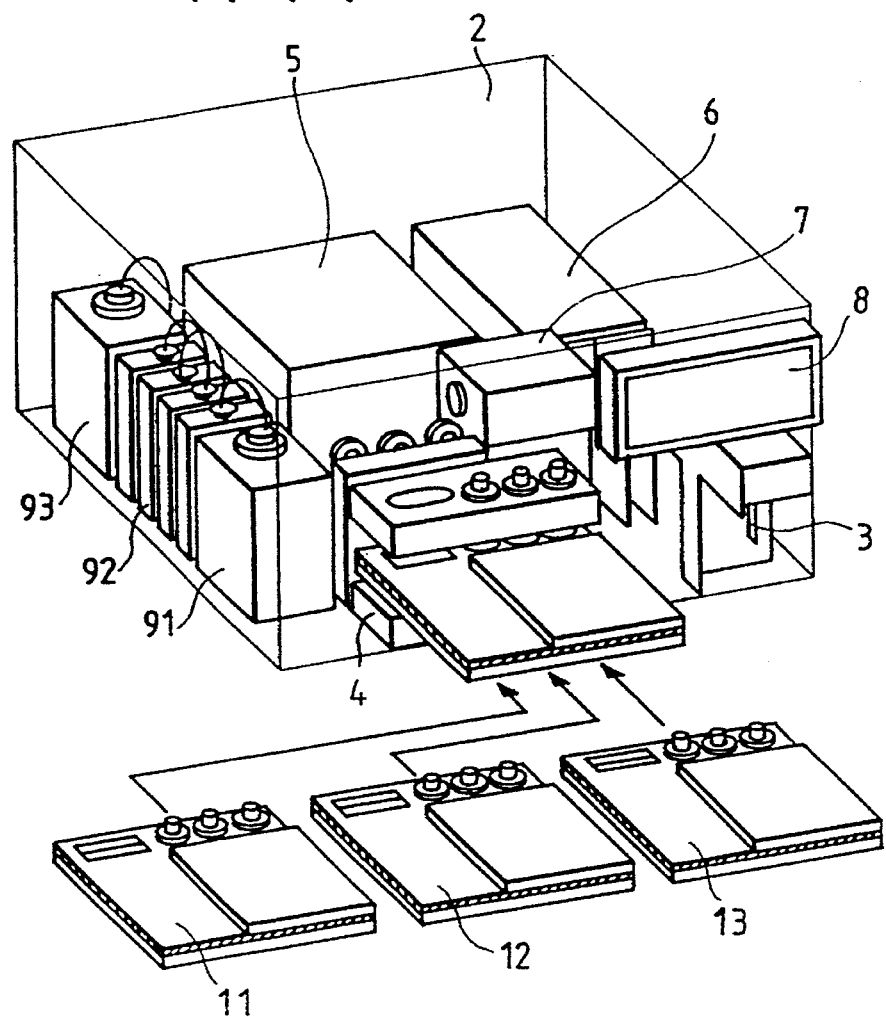
FIG. 1 is a perspective view illustrating a composition of an apparatus for chemical analysis in the first embodiment of the present invention.
Figure 2:
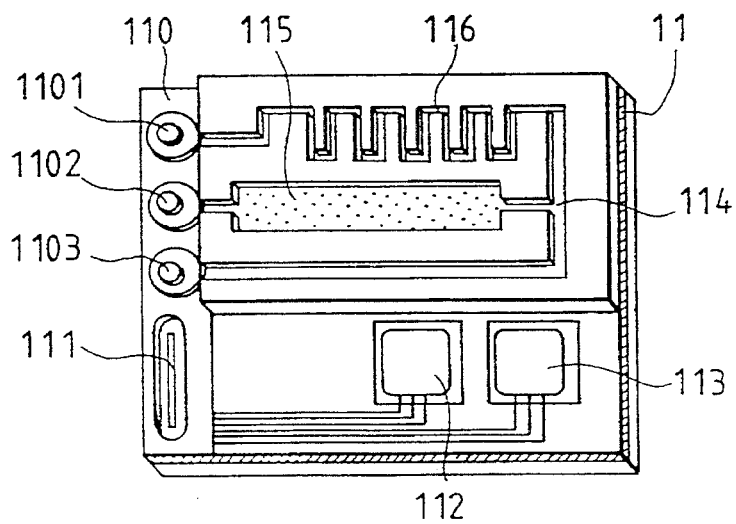
FIG. 2 is a perspective view illustrating a composition of a chemical analytical unit mounted on the apparatus for chemical analysis shown in FIG. 1.
Figure 3:
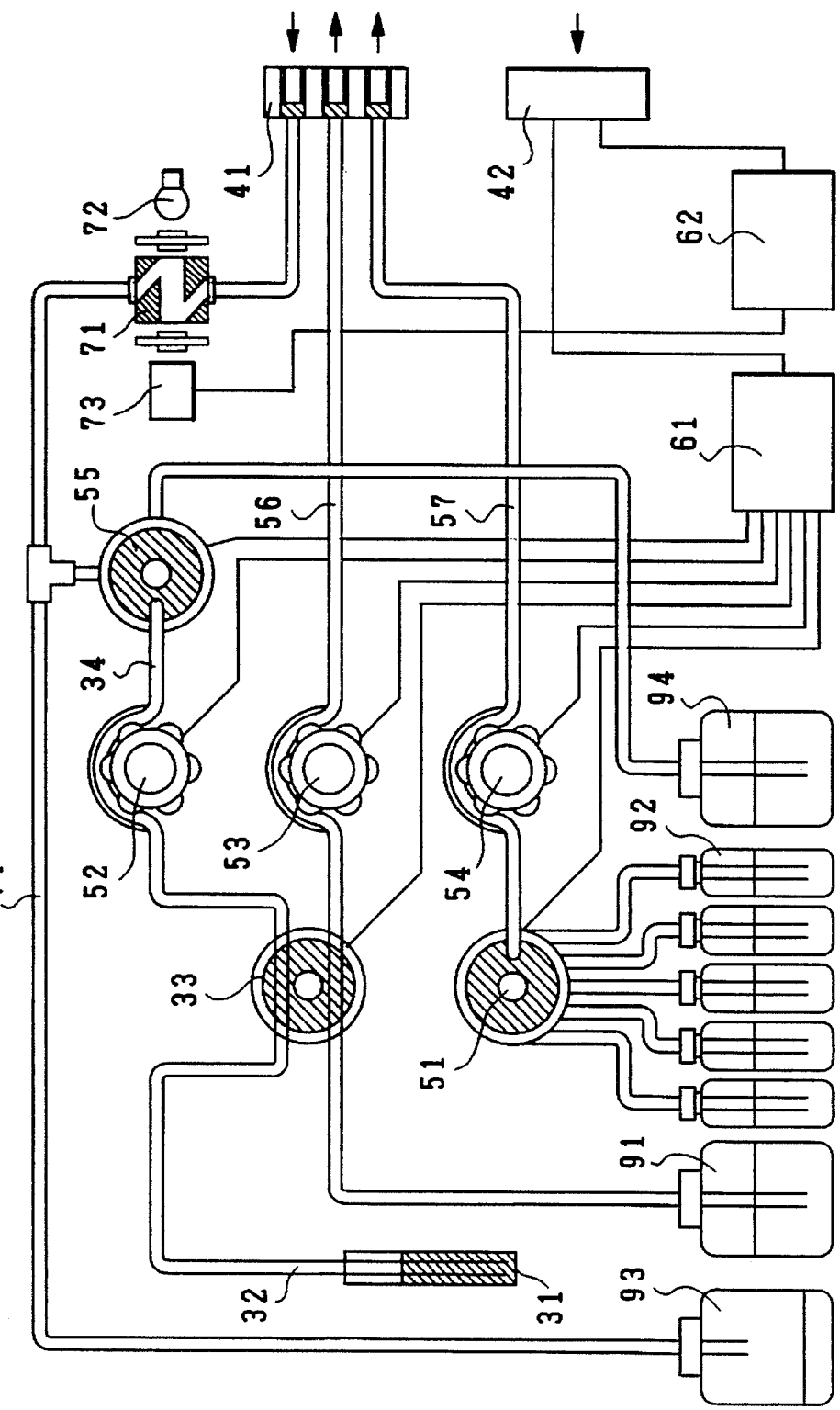
FIG. 3 is a flow diagram in the main body of the apparatus for chemical analysis.
Figure 4:
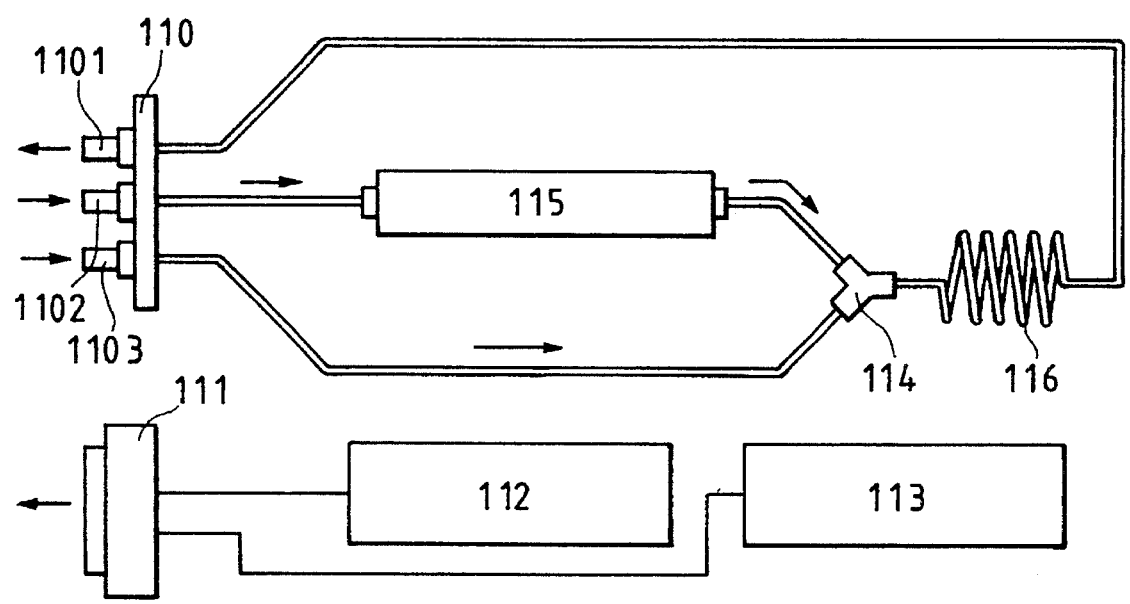
FIG. 4 is a flow diagram in the chemical analytical unit.
Figure 5:
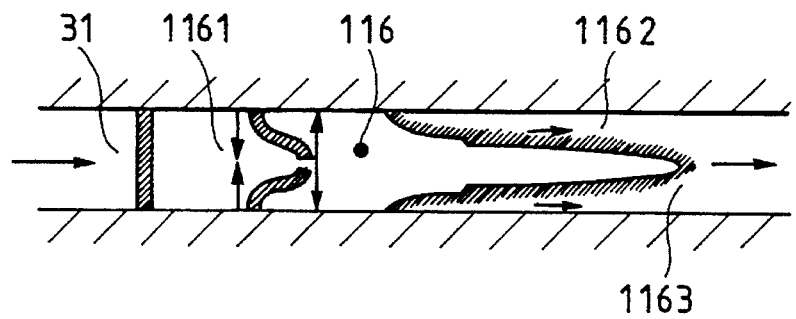
FIG. 5 is an illustration for explaining mixing principle of flow injection.
Figure 6:
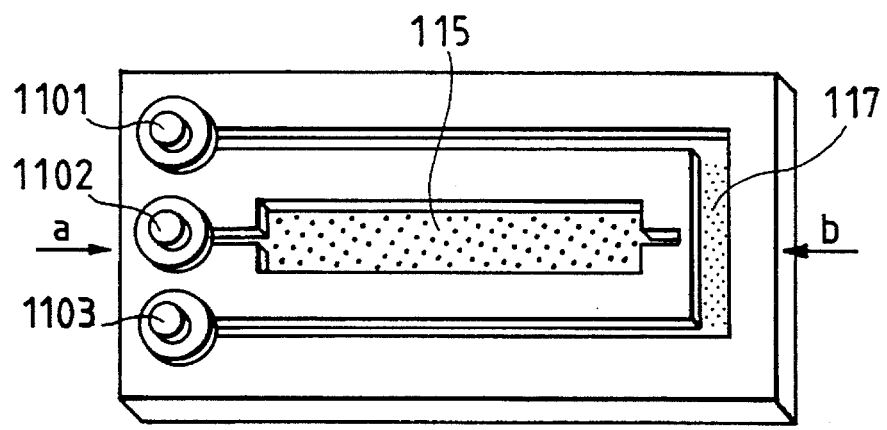
FIG. 6 is a perspective view illustrating a composition of mixing portion in the chemical analytical unit when utilizing micromixer.
Figure 7:
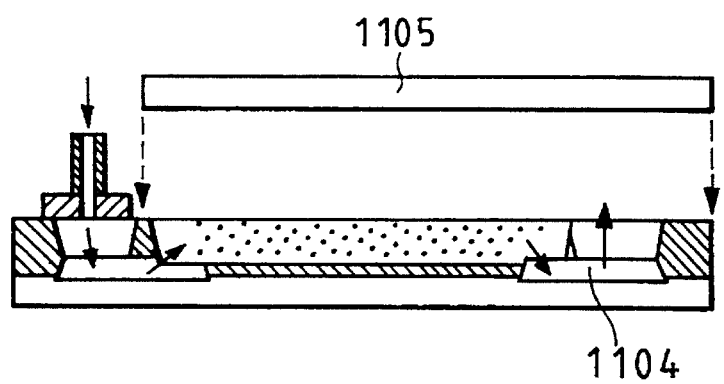
FIG. 7 is a vertical cross section illustrating a composition of mixing portion in the chemical analytical unit when utilizing micromixer.
Figure 8:
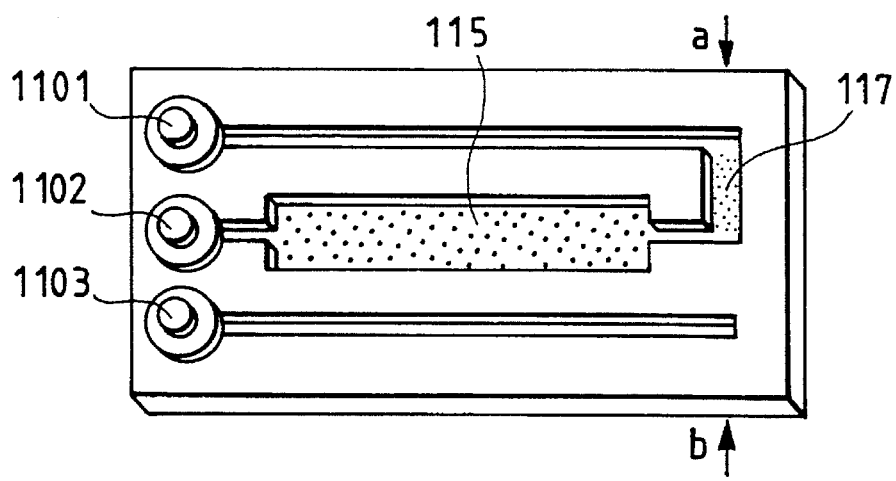
FIG. 8 is a perspective view illustrating a composition of mixing portion in the chemical analytical unit when utilizing micromixer.
Figure 9:
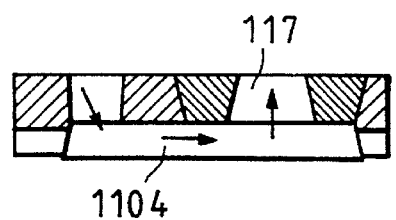
FIG. 9 is a vertical cross section illustrating a composition of mixing portion in the chemical analytical unit when utilizing micromixer.
Figure 10:
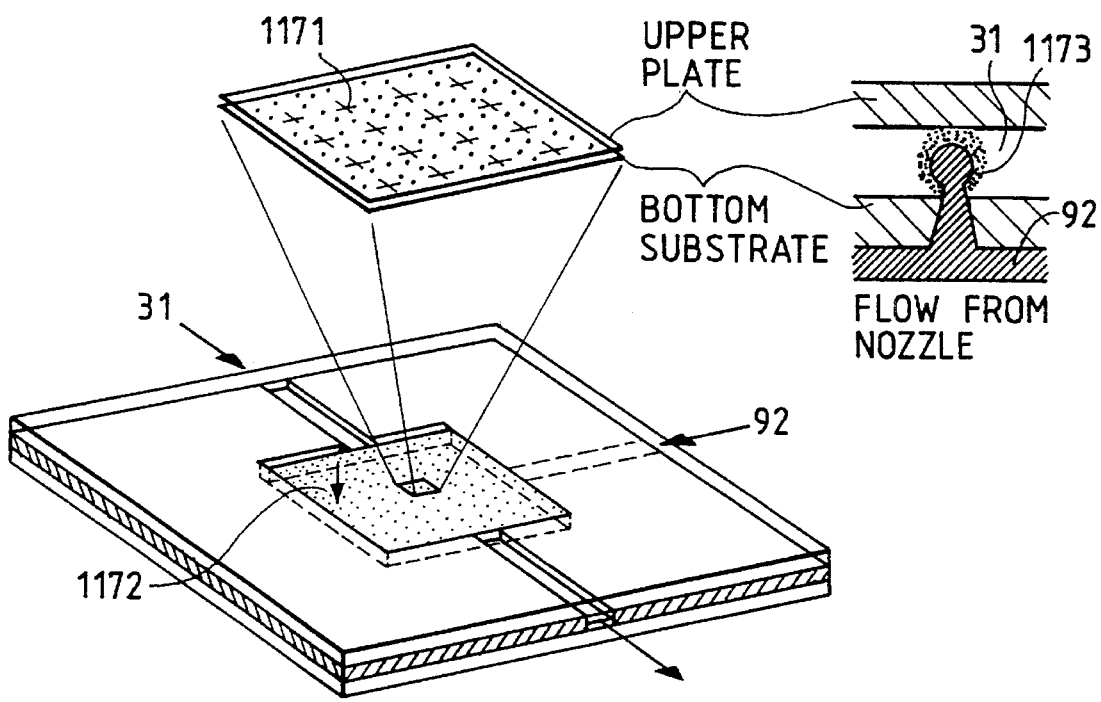
FIG. 10 is a perspective view for explaining mixing principle of a micromixer.

The first embodiment of the present invention is explained referring to FIGS. 1–10. FIG. 1 is a perspective view illustrating a composition of an apparatus for chemical analysis in the present embodiment, FIG. 2 is a perspective view illustrating a composition of a chemical analytical unit mounted on the apparatus for chemical analysis shown in FIG. 1, FIG. 3 is a flow diagram in the main body of the apparatus for chemical analysis, FIG. 4 is a flow diagram in the chemical analytical unit, FIG. 5 is an illustration for explaining mixing principle of flow injection, FIGS. 6–9 are illustrations indicating composition of a mixing portion in the chemical analytical unit when utilizing micromixer disclosed in a reference, ("Micro Mixer with Fast Diffusion", Proc. of MEMS' 93 (1993)), FIG. 6 is a perspective view, FIG. 7 is a vertical cross section, FIG. 8 is a perspective view, FIG. 9 is a vertical cross section, and FIG. 10 is a perspective view for explaining mixing principle of the micromixer.

Composition of the present embodiment is explained referring to FIGS. 1–4. As shown in FIG. 1, the apparatus for chemical analysis relating to the present embodiment comprises mainly a main body of analytical apparatus 2 and chemical analytical units 11–12. The main body of the analytical apparatus comprises a sampling portion 3, liquid and signal connectors 4, a liquid controlling portion 5, a controller 5, a signal processor 6, a detector 7, a display portion 8, and liquid vessels for storing carrier liquid 91, reagents 92, and washing liquid 93.

As shown in FIG. 2, the analytical unit 11 has a connector for liquids 110 and a connector for electrical signals 111, both of which are connected to the liquid and signal connector 4 in the main body of the analytical apparatus 2. In the present embodiment, the liquid connector 110 has three connectors such as a connector for reagent supply 1103, a connector for sample liquid 1102, and a connector for transferring mixed and reacted sample 1101 to the main body of the analytical apparatus 2. In order to mix a plurality of reagents to sample, a plurality of connectors for reagent supply 1103 are provided. A chromatocolumn 115 for separating components in the sample is connected to the connector for sample liquid 1102, and outlet of the chromatocolumn 115 is merged with a flow path extended from the connector for reagents 1103 to form a flow path (The merging portion of the flow path is called hereinafter as "an injection portion 114" for convenience). A mixing flow path 116 is provided at downstream side of the injection portion 114, and downstream side of the mixing flow path 116 is connected to the connector for reacted liquid 1101. Signal wires from two memories 112, 113 are connected to the signal connector 111 in the analytical unit 11. Adequate samples for analytical methods, amounts, flow rate, and mixing timing of reagents and others are stored in one of the memories 113. In another memory 112, setting methods for measuring conditions and processing methods of data and others are stored.

Each of elements in the main body of the analytical apparatus 2 is connected as shown in FIG. 3. Flow paths can be divided roughly into four flow systems such as a flow system for sucking samples 34, a flow system for transferring samples 56, a flow system for supplying reagents 57, and a flow system for measuring samples 74.

In the flow system for sucking samples 34, a sample sucking pipe 32, a sampling valve 33, a pump for sucking sample 52, and switching valve for changing drainage and clean up 55 are arranged in order from sample 31 side. In the flow system for transferring samples 56, a vessel for carrier liquid 91, a sampling valve 33, and a pump for transferring sample 53 are arranged in order from carrier liquid 91 side. In the flow system for supplying reagents 56, a vessel for reagents 92, a switching valve for changing supplying regents 51, and a pump for supplying reagents 54 are arranged in order from reagents 92 side. In the flow system for measuring samples 74 after reactions, a detecting flow cell 71 and a vessel for waste liquid 93 are arranged. The signal connector in the main body of the analytical apparatus 2 is connected to a signal processor 62 and pump-valve controller 61, and the signal processor 62 is connected to a detector 73. And, the pump-valve controller 61 is connected to pumps 52, 53 and valves 51, 33, 55.

Operation of the apparatus for chemical analysis of the present embodiment composed as above is explained hereinafter. First, an analytical unit 11 suitable for analytical items to be measured is selected, and supplied and fixed to the main body of the analytical apparatus 2. At that time, the liquid connector 110 and the signal connector 111 of the analytical unit 11 are connected to the liquid signal connector 4 in the main body of the analytical apparatus 2. Subsequently, the pump-valve controller 61 and the signal processor 62 in the main body of the analytical apparatus 2 start to operate, and take in signals describing processing steps, analytical methods, and data processing method of samples from the memories 112, 113 in the analytical unit 11 through the signal connector 111.

In accordance with the supplied processing steps, flow of liquid is controlled as explained hereinafter. First, a designated amount of sample 31 is taken by the sampling pipe 32. Then, the pump for sucking sample 52 sucks the taken sample 31 to a position of sampling valve 33. Subsequently, the sampling valve 33 operates to take a designated amount of sample 31 and supplies the sample 31 into carrier liquid in the flow system for transferring sample 56. Further, the pump for transferring sample 53 operates to transfer the carrier liquid containing the sample into a chromatocolumn 115 in the analytical unit 11 through the liquid connector 41. The chromatocolumn 115 separates the sample 31 into components, and the separated sample is transferred to the injection portion 114. Sequentially with the above moving of the sample, the pump for transferring reagents 54 and the switching valve for changing reagents 51 operate under flow conditions such as flow rates and merging timing which are stored in the memory 113, and supply designated reagents 92 in the vessel for reagents 92 to the injection portion 114 in the analytical unit 11 through the liquid connector 41.

At the injection portion 114, the sample and the reagent are merged and transferred to subsequent mixing flow path 116. In the mixing flow path 116, the sample and a designated amount of the reagent are mixed and reacted. Pumps 53, 54 transfer the reacted sample into the main body of the analytical apparatus through the liquid connector 1101 again, and further supply the sample to a detecting flow cell 71. A light irradiation means 72 and an detector 73 measure the sample in accordance with setting conditions such as absorbing spectrum range and time stored in the memory 112. A signal processor 62 reads measured results from the detector 73, performs data processing of the sample in accordance with a designated data processing method stored in the memory 112, and supplies results of the data processing to a display portion 8 for displaying.

Mixing of the sample with the reagent at the mixing flow path 116 is performed by both counter current 1162 in a flowing direction and molecular diffusion 1161 in a perpendicular direction to the flow as shown in FIG. 5. Mixing flow combined the above two phenomena is called as Taylor diffusion. As for other mixing means, a micro mixer disclosed in the reference ("Micro Mixer with Fast Diffusion" Proc. of MEMS' 93 (1993) IEEE) can be utilized. Principle of the micro mixer 117 is, as shown in FIG. 10, in distributing a large number of micro nozzles 1171 densely in wall of a mixing portion 1172, and mixing two liquids by spouting one liquid from the micro nozzles 1171 into another liquid in the mixing portion 1172.

Flow paths can be composed utilizing the micro mixers 117 as shown in FIGS. 6–9. In the composed flow paths shown in FIGS. 6, 7, two liquids are mixed by spouting sample which is separated by the chromatocolumn 115 into a reagent flow path. Otherwise, two liquids can be mixed by spouting the reagent into the separated sample as shown in FIGS. 8, 9.

The apparatus for chemical analysis relating to the present embodiment can analyzes various analytical items without changing connection of flow paths and analytical elements which have required significant man-hour hitherto, because analytical units 11–13 for each of analytical items, wherein analytical elements and flow paths required for the each of analytical items are arranged, are provided previously. Further, as detailed flow conditions, analytical methods, and data processing methods for analysis are stored in the analytical units, the apparatus for chemical analysis relating to the present embodiment can be operated and used for analysis without special knowledge.

Embodiment 2

Figure 11:
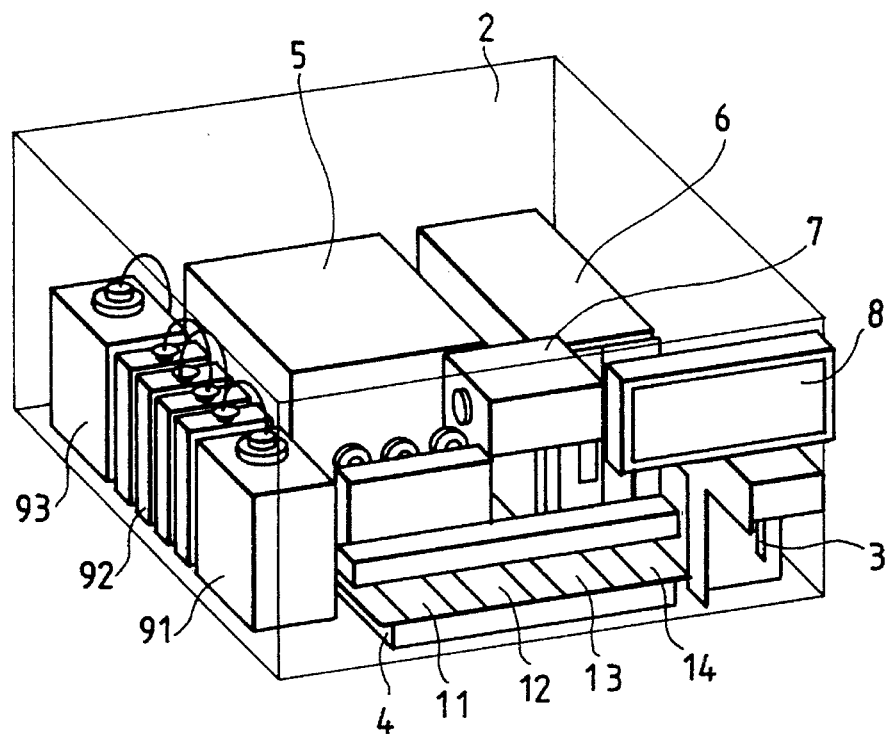
FIG. 11 is a perspective view illustrating a composition of the second embodiment of the present invention.
Figure 13:
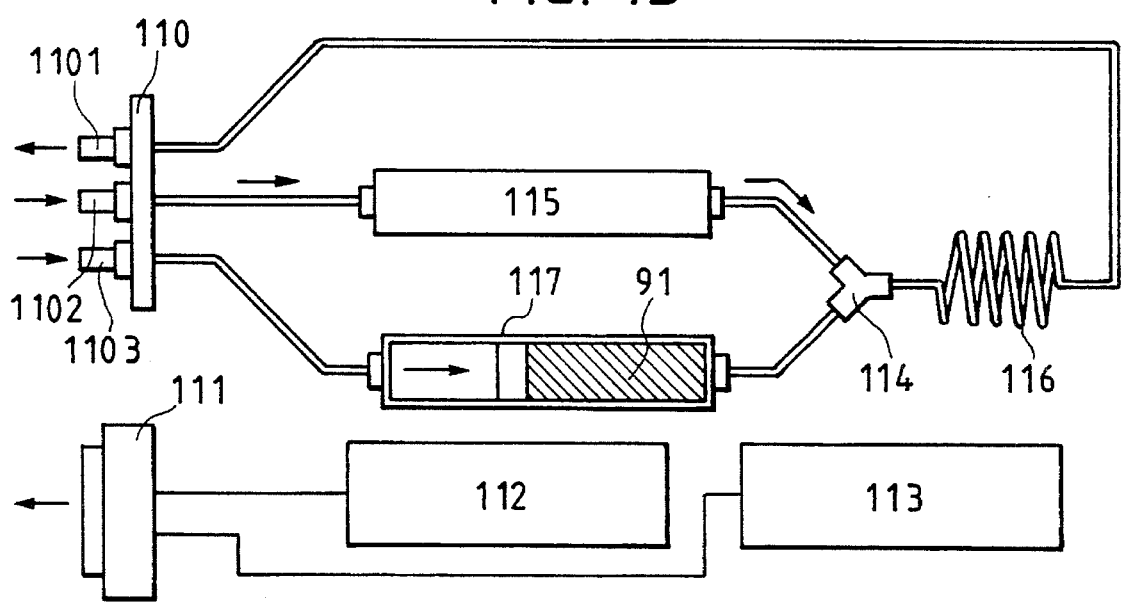
FIG. 13 is a flow diagram in the analytical unit of the apparatus for chemical analysis shown in FIG. 11.
Figure 12:
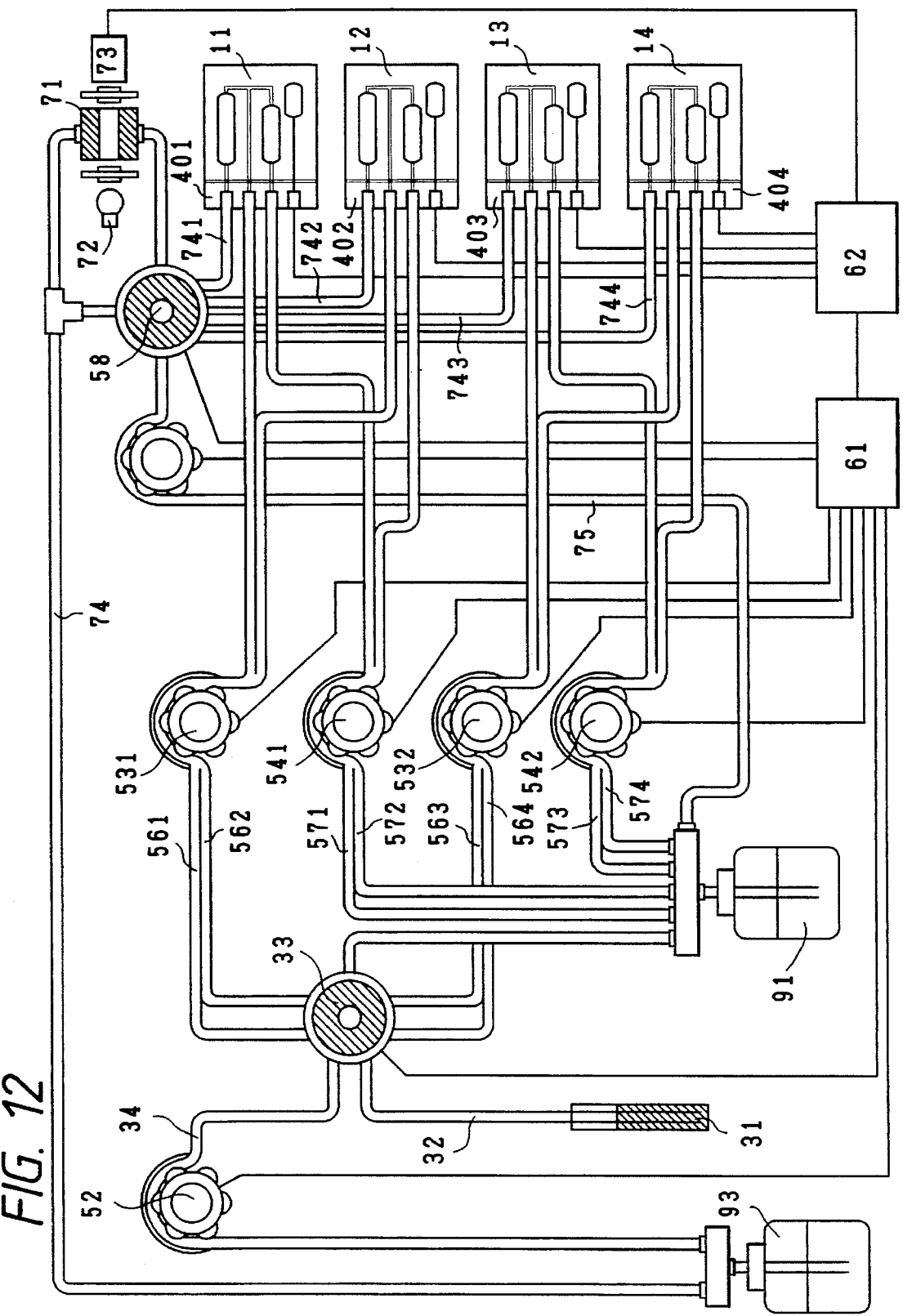
FIG. 12 is a flow diagram in the apparatus for chemical analysis shown in FIG. 11.

The second embodiment of the present invention is explained hereinafter referring to FIGS. 11–14. FIG.11 is a perspective view illustrating a composition of the present embodiment, FIG. 12 is a flow diagram in the apparatus for chemical analysis shown in FIG. 11, FIG. 13 is a flow diagram in the analytical unit of the apparatus for chemical analysis shown in FIG. 11, and FIG. 14 is an illustration for explaining operation principle of the apparatus for chemical analysis shown in FIG. 11.

The apparatus for chemical analysis of the present embodiment is so composed that plural analytical units can be connected to the apparatus simultaneously in order to analyze plural analytical items on a sample concurrently or in a short time. Therefore, the apparatus is composed, as shown in FIG. 11, of four analytical units 11, 12, 13, 14, a liquid-signal connector 4 for the four analytical units, a sampling portion 3, a liquid controlling portion 5, a signal processor 6, a detector 7, a display portion, and liquid vessels 91–94.

Referring to the flow diagram shown in FIG. 12, compositions of each elements are explained hereinafter.

Flow paths can be divided roughly into four flow systems such as a flow system for sucking samples 34, flow systems for transferring samples 561, 562, 563, 564, flow systems for operating liquid for supplying reagents 571, 572, 573, 574, and flow systems for measuring reacted samples 741, 742, 743, 744.

In the flow system for sucking samples 34, a sample sucking pipe 32, a sampling valve 33, a pump for sucking sample 52, and a vessel for waste liquid 93 are arranged in order from sample 31 side. The flow systems for transferring samples 561, 562, are provided with a pump for transferring sample 531, and are connected to the analytical units 11, 12, through the liquid-signal connectors 41, 42.

The flow systems for supplying sample 563, 564, are provided with a pump for supplying sample 532, and are connected to the analytical units 13, 14, through the liquid-signal connectors 43, 44. The flow systems for operating liquid for supplying reagents 571, 572, are provided with a pump for operating liquid for supplying reagents 541, and are connected to the analytical units 11, 12, through the liquid-signal connectors 41, 42. The flow systems for operating liquid for supplying reagents 573, 574, are provided with a pump for operating liquid for supplying reagents 542, and are connected to the analytical units 13, 14, through the liquid-signal connectors 43, 44.

Further, flow paths 741–744 are formed and extended from each of the analytical units to a reacted sample distributing valve 58 through the liquid-signal connector 4. After the distributing valve 58, a flow cell for detecting 71 is connected. At flow paths for operating liquid for supplying reagents in each of analytical units, syringes 117 containing reagents as shown in FIG. 13 are provided. A piston is arranged in the syringe, and a designated reagent is filled in one side of the piston and operating liquid is filled in another side of the piston.

Referring to FIGS. 12–14, operation of the apparatus for chemical analysis of the present embodiment composed as above is explained hereinafter.

First, analytical units 11–14 for desired analytical items are selected, and fixed to the main body of the analytical apparatus 2. At that time, the liquid-signal connectors 41, 42, 43, 44 are connected collectively to the connector 4 in the main body of the analytical apparatus 2. Subsequently, the pump-valve controller 61 and the signal processor 62 in the main body of the analytical apparatus 2 start to operate, and take in signals describing processing steps, analytical methods, and data processing method of samples for each analytical items from the memories 112, 113, 122, 123, 132, 133, 142, and 143 in the analytical units 11–14 through the signal connectors 41, 42, 43, 44.

In accordance with the supplied processing steps, a pump for sucking sample 52 starts to operate, and takes a designated amount of sample 31 by the sampling pipe 32. Then, a sampling valve 33 operates to supply a part of sample into the flow path for transferring sample 561. Further, the pump for transferring sample 531 operates to transfer the sample into the analytical unit 11 in accordance with designated flow conditions such as a flow rate, a timing stored in the memory 113 of the analytical unit. Simultaneously, a pump for operating liquid for supplying reagents 541 operates according to a designated conditions, and supplies operating liquid to the analytical unit 11 in order to move the piston in the reagent syringe 117 in the analytical unit to spout the reagent out from the syringe.

The sample and the reagent are merged at an injection portion, mixed and reacted at the mixing flow path 116, returned to the main body of the apparatus 2 again through the liquid connector 41, and arrives at the distributing valve 58 through the flow path 741. The memory 113 stores arriving time of the sample at the valve, and the distributing valve 58 receives the arriving time and switches the flow of the reacted sample from the flow path for waste liquid 74 to the flow path to the detecting flow cell 71 at preferable timing with the arriving time.

While the mixing and the reaction are performed in the analytical unit by operating the pump for transferring sample 531 and the pump for operating liquid for supplying reagents 541, carrier liquid and operating liquid for supplying reagents are also supplied to the analytical unit 12 concurrently, and the above liquids are used for cleaning of flow paths in the analytical unit 12.

Subsequently, the sampling valve 33 operates again after a designated time to supply other sample remained in the valve to other flow path for sample carrier liquid 563. The above sample is transferred further to the analytical unit 13, and mixed and reacted with reagent after a designated delay time. The mixing and the reaction at each of the analytical units are repeated in an order of the analytical units 11, 13, 12, 14, 11 as shown in FIG. 14. Because of the operation as described above, each of the analytical units does not interfere each other at the detecting flow cell 71. Consequently, various analysis on a sample can be performed successively as shown in FIG. 14.

Embodiment 3

Figure 15:
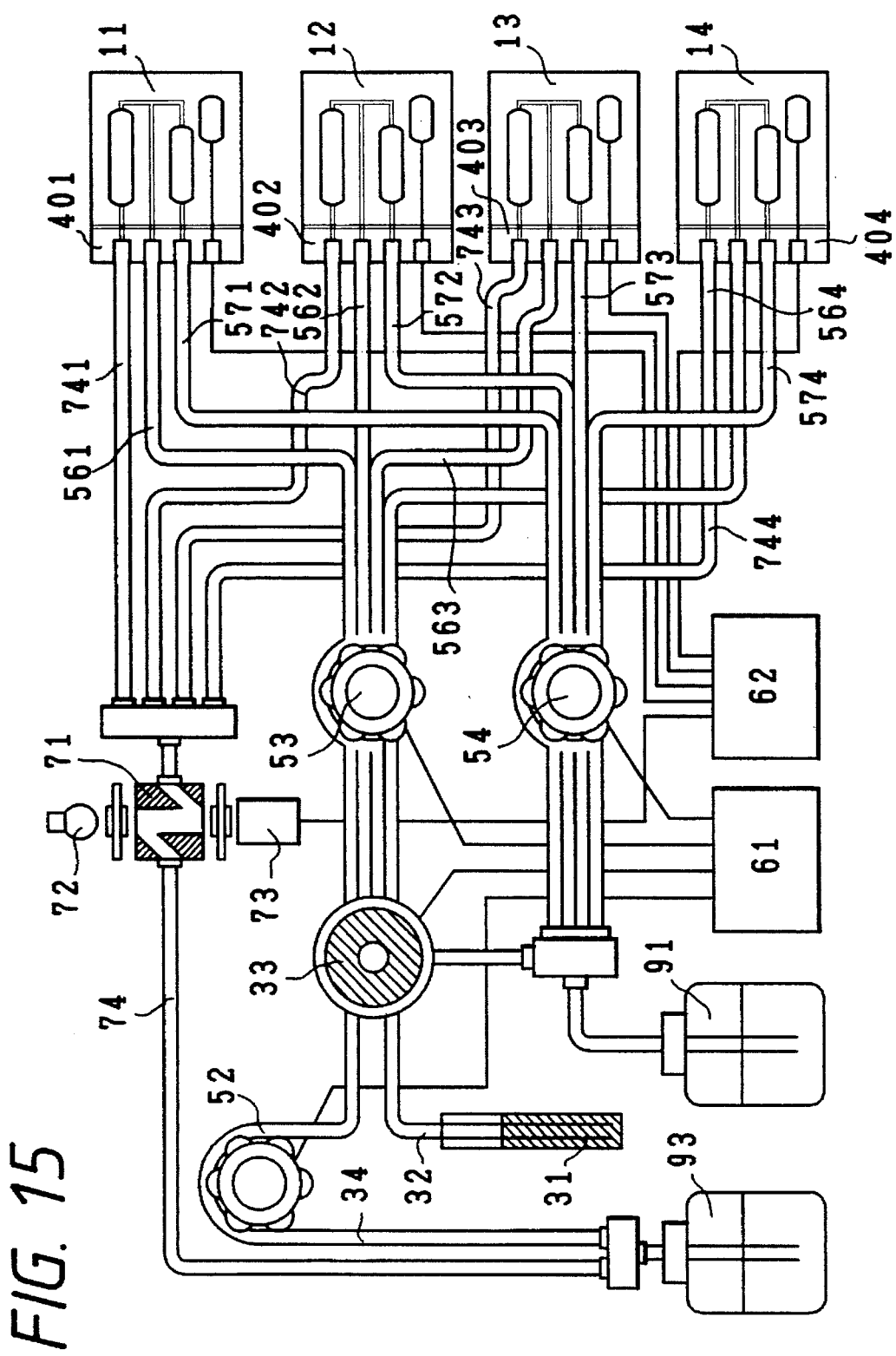
FIG. 15 is a flow diagram in the apparatus for chemical analysis of the third embodiment of the present invention.
Figure 16:
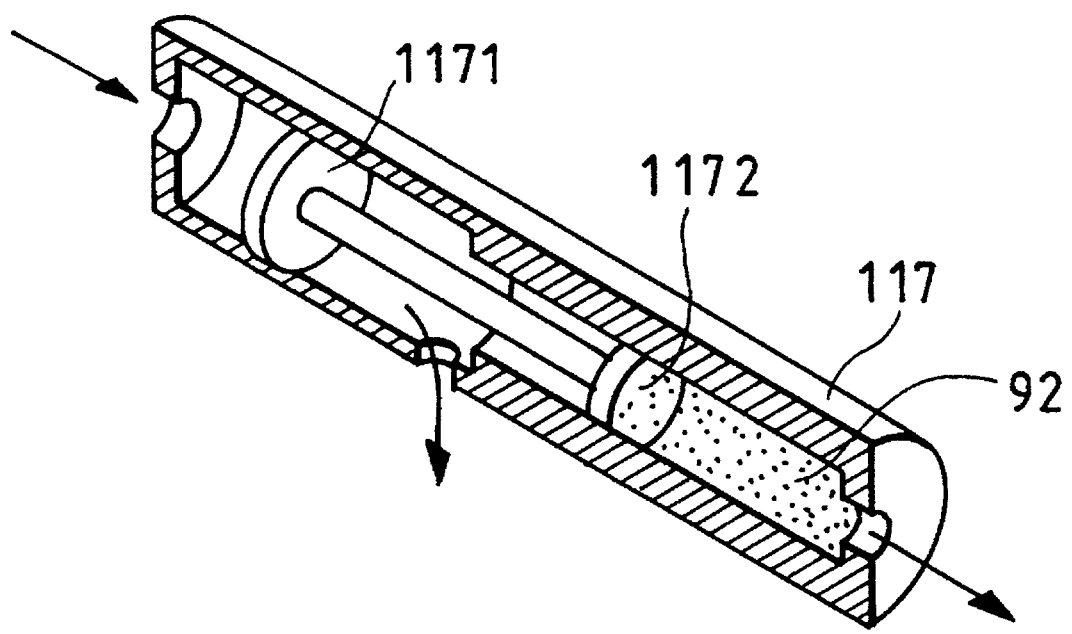
FIG. 16 is a perspective cross section illustrating a structure of a reagent syringe in the analytical unit.

The third embodiment of the present invention is explained hereinafter referring to FIGS. 15–17. FIG. 15 is other flow diagram in the apparatus for chemical analysis shown in FIG. 11, FIG. 16 is a perspective cross section illustrating a structure of a reagent syringe in the analytical unit used in the above case, and FIG. 17 is an illustration for explaining operation principle of the apparatus for chemical analysis shown in FIG. 15. In the present embodiment, the apparatus for chemical analysis is provided with plural analytical units as same as the embodiment 2, and composed so as to analyze plural analytical items concurrently.

In the present embodiment, as shown in FIG. 15, flow paths can be divided roughly into four flow systems such as a flow system for sucking samples 34, flow systems for transferring samples 561, 562, 563, 564, flow systems for operating liquid for supplying reagents 571, 572, 573, 574, and flow systems for measuring reacted samples 741, 742, 743, 744. In the flow systems for transferring samples and the flow systems for operating liquid for supplying reagents are provided with pumps for transferring liquid 53, 54. A syringe 171 for reagents provided in each of the analytical units 11–14 has a structure shown in FIG. 16. In the syringe, a stroke of a first piston is designated by an amount of operating liquid for reagent supplied from left side of the syringe, and a designated amount of reagent is spouted by moving of a second piston connected to the first piston in the syringe.

Operation of the apparatus for chemical analysis of the present embodiment composed as above is explained hereinafter.

First, a pump for sucking sample 52 starts to operate, and takes a designated amount of sample 31 by the sampling pipe 32. Then, a sampling valve 33 operates to supply a designated amount of samples into each of flow path for transferring sample. The pump for transferring sample 53 operates to transfer each of the samples into each of the analytical units in accordance with designated flow conditions. Simultaneously, a pump for operating liquid for supplying reagents 54 operates according to a designated conditions, and supplies operating liquid to each of the analytical units. Because the syringes for reagents in each of the analytical units has such a structure as shown in FIG. 16, supplying amount of reagents can be controlled based on contents of analysis. On account of difference in respective lengths of flow paths 741–744 from each of the analytical units to the detecting flow cell 71, a required time for each of samples transferring from each of the analytical units to the flow cell differs respectively, and consequently, each sample from each of analytical units does not interfere mutually at the flow cell position. The above operation steps are repeated as shown in FIG. 17.

As explained in the above embodiments 1 and 2, the analytical unit to be connected to the main body of the analytical apparatus is prepared for each of analytical items, and samples taken successively are distributed to respective analytical units and determined respectively. Accordingly, it is possible to process plural reactions for plural analytical items concurrently or in a short time. Consequently, simultaneous chemical analysis of multi-items which could not performed by conventional flow type apparatus for chemical analysis has become possible by the present invention.

Further, in either of the above embodiments 1 and 2, liquid controlling means such as pumps, valves, sampling pipes and others provided in the main body of the analytical apparatus can be loaded in the analytical unit respectively. In this case, the main body of the analytical apparatus has a role to receive samples processed in the analytical units and to detect the samples by the detector. By altering the present invention as described above, more easy-to-use apparatus can be provided, and down-sizing of the main body of the analytical apparatus becomes possible. Furthermore, on account of shortening flow paths, required amount of reagents and samples can be decreased.

By loading the detector in the analytical unit, significant shortening of flow paths becomes possible, and down-sizing of whole apparatus and remarkable decreasing in required amount of liquid can be achieved.

In any of the above embodiments 1, 2, and 3, if wire electrical discharging and/or lithographic technique are used in manufacturing the analytical unit, especially members such as the mixing flow path, micro nozzles, chromatocolumn, and others, the members can be fabricated precisely and in small sizes. Accordingly, down-sizing of the analytical unit is facilitated using precise micro work techniques, and productivity can be improved remarkably.

As explained above, in accordance with the apparatus for chemical analysis relating to the present invention, firstly, the analytical units are prepared for respective analytical items, and members such as analytical elements and flow paths are composed so as to be suitable for the analytical items. Accordingly, changing connections of flow paths and analytical elements, which required a large amount of man-hours hitherto, can be eliminated.

Second, detailed flow conditions, analytical methods, and data processing methods for analysis are stored in the analytical unit, and consequently, the apparatus for chemical analysis which is operable and capable of the analysis without special knowledge can be provided.

Third, the analytical unit to be connected to the main body of the analytical apparatus are prepared respectively for each of analytical items, samples taken successively are distributed to respective analytical units, and reaction processing for multi-items can be performed concurrently or in a short time. Consequently, the apparatus for chemical analysis capable of performing chemical analysis on a large amount of samples for multi-items, which have been difficult by conventional apparatus for chemical analysis, can be provided.

What is claimed is:

1. An analytical apparatus for chemical analysis comprising;
   a main body of the analytical apparatus having:
      a sampling means for sucking samples,
      a liquid controlling means for transferring the sucked samples and reagents, and
      a detecting means for measuring samples, and
   an analytical unit having:
      a liquid connector to be connected to said main body of the analytical apparatus,
      an electrical signal connector to be connected to said main body of the analytical apparatus, and
      a memory means storing at least an analytical method, wherein said sample is analyzed by
      attaching said analytical unit to said main body of the analytical apparatus,
      transferring said analytical method stored in said memory means to said main body of the analytical apparatus, and
      analyzing said sample in accordance with said transferred analytical method.

2. An apparatus for chemical analysis as claimed in claim 1, wherein said analytical unit is arranged corresponding to said analytical method including at least one separating and purifying means suitable for analytical items.

3. An apparatus for chemical analysis as claimed in claim 1, wherein said main body of the analytical apparatus is provided with:
   a detector for measuring the sample processed by said analytical unit,
   a signal connector for transmitting data observed at said detector, and
   a signal processor for receiving observed data from said analytical unit through said signal connector, and processing said observed data in accordance with data processing method suitable for analytical items.

4. An apparatus for chemical analysis as claimed in claim 1, wherein said analytical unit is provided with mixing and reacting means comprising:
   a flow path for reagent,
   a flow path for sample,
   a merging portion of the above two flow paths, and
   a flow path for mixing successive to said merging portion.

5. An apparatus for chemical analysis as claimed in claim 1, wherein said analytical unit is provided with separating and purifying means, and said separating and purifying means is chromatocolumn.

6. An apparatus for chemical analysis as claimed in claim 1, wherein said analytical unit is provided with a flow path for reagent and a flow path for sample, one of which is provided with a large number of micro nozzles at wall plane of the flow path, and mixing and reacting means composed of a merging portion where the above two flow paths are merged through said micro nozzles.

7. An apparatus for chemical analysis as claimed in claim 1, wherein said main body of the analytical apparatus is provided with:
   a connector for connecting a plurality of analytical units,
   a liquid controlling means for controlling flow of liquid in respective analytical units through said connector,
   a controller for reading out contents stored in memory means in said plural analytical units and controlling said liquid controlling means and said detecting means for respective analytical items in accordance with the reading out contents, and
   a signal processor for reading out processing methods of observed data stored in memory means in said plural analytical unit and processing the observed data.

8. An apparatus for chemical analysis as claimed in claim 1, wherein said main body of the analytical apparatus is provided with:
   a memory portion storing sample processing steps and observed data corresponding to plural analytical items,
   a controller for reading out signals from said memory portion and controlling said liquid controlling means and said detecting means, and
   a signal processor for reading out processing methods of observed data stored in said memory portion and processing the observed data.

9. An apparatus for chemical analysis as claimed in claim 1, wherein a whole or a part of said analytical unit is manufactured integrally by precise micro work.

10. An apparatus for chemical analysis as claimed in claim 1, wherein said signal connector transmits at least any signal selected from a group of electric signal, magnetic signal, optical signal, and physical signal.

11. An analytical apparatus for chemical analysis comprising;
   a main body of the analytical apparatus, and
   an analytical unit having:
      a memory means storing analytical processing steps and processing method for observed data, wherein
   said main body of the analytical apparatus comprises:
      a sampling means for sucking samples,
      a liquid controlling means for transferring sucked samples and reagents,
      a detecting means for measuring samples,
      a controller for reading out the analytical processing steps stored in the memory means of the analytical unit through a signal connector in the analytical unit, and controlling said sampling means, said liquid controlling means, and detecting means in accordance with the read out analytical processing steps, and
      a signal processor for reading out the processing method for the observed data stored in the memory means in the analytical unit, and
   analysis of the sample is performed by attaching said analytical unit to said main body of the analytical apparatus.

12. An analytical apparatus for chemical analysis comprising;
   a main body of the analytical apparatus having:
      a sampling means for sucking samples,
      a liquid controlling means for transferring the sucked samples and reagents, and
      a detecting means for measuring samples, and
   an analytical unit having:
      a liquid connector to be connected to said main body of the analytical apparatus,
      a signal connector to be connected to said main body of the analytical apparatus,
      a memory means storing at least an analytical method, and
      a mixing means for mixing said sample with reagent, wherein
   said liquid connector has respective connectors for sample, reagent, and mixed and reacted sample, and
   said sample is analyzed by a method comprising the steps of:
      attaching said analytical unit to said main body of the analytical apparatus,
      transferring said sample and reagent to the analytical unit through said liquid connector,
      mixing said sample and the reagent in accordance with analytical method stored in said memory means,
      transferring the mixed and reacted sample to the detecting means in said main body of the analytical apparatus, and
      measuring said mixed and reacted sample by the detecting means.

13. An analytical apparatus for chemical analysis comprising;
   a main body of the analytical apparatus having:
      connectors for plural analytical units,
      a sampling means for sucking samples,
      a liquid controlling means for transferring the sucked samples and reagents, and
      a detecting means for measuring samples, and
   a plurality of analytical units having:
      memory means for storing processing methods to process each analytical items prepared for each different analytical items, wherein:
   a sample is analyzed on plural different analytical items by:
      reading out the processing methods stored in said memory means in the analytical units through signal connectors, and
      controlling said sampling means, said liquid controlling means, and said detecting means in accordance with the processing methods.

14. An apparatus for chemical analysis as claimed in claim 13, wherein said main body of the analytical apparatus is provided with a signal connector for receiving driving signal for controlling operation of the liquid controlling means and the detector from the analytical unit.

15. An analytical apparatus for chemical analysis comprising;
   a main body of the analytical apparatus having:
      a sampling means for sucking samples,
      a liquid controlling means for transferring the sucked samples and reagents, and
      a detecting means for measuring samples, and
   an analytical unit having:
      memory means for storing analytical processing steps and processing methods of observed data,
      a liquid connector to be connected to said main body of the analytical apparatus, and
      a signal connector to be connected to said main body of the analytical apparatus, wherein:
   analysis of the samples is performed by:
      attaching said analytical unit to said main body of the analytical apparatus,
      transmitting signals mutually between said analytical unit and said main body of the analytical apparatus, and
      transferring said sample and reagents mutually between said analytical unit and said main body of the analytical apparatus.

16. An analytic apparatus for chemical analysis comprising;
   a main body of the analytical apparatus, and
   an analytical unit having:
      at least one mixing and reacting means,
      a liquid connector for transferring samples and reagents,
      flow paths piped and arranged for connecting said liquid connector corresponding to methods for chemical analysis suitable for analytical items,
      memory means for storing processing steps of the samples and processing methods of observed data, and
      a signal connector for transmitting stored content in said memory means, wherein:
   analysis of the samples is performed by:
      attaching said analytical unit to said main body of the apparatus for chemical analysis, and
      controlling members provided in said main body of analytical apparatus in accordance with said processing steps of the samples and said processing methods of observed data.

17. An analytic apparatus for chemical analysis comprising;
   a main body of the analytical apparatus having:
      a sampling means for sucking samples,
      a liquid controlling means for transferring the sucked samples and reagents, and
      a detecting means for measuring samples,
      a controller for reading out analytical processing steps stored in memory means in an analytical unit through a signal connector and controlling said sampling means, said liquid controlling means, and said detecting means, and
      a signal processor for reading out processing methods of observed data stored in memory means in the analytical unit and processing the observed data, and
   a plurality of analytical unit having:
      memory means for storing analytical processing steps of different analytical items and processing methods of observed data, wherein:
   said main body of analytical apparatus is composed to be attached with said plural analytical units, and
   analysis of the samples is performed by:
      attaching said plural analytical units to said main body of analytical apparatus, and
      controlling said sampling means, said liquid controlling means, and said detecting means so that analytical processing of each analytical items does not interfere mutually.

18. An analytical apparatus for chemical analysis comprising;
   a main body of the analytical apparatus having:
      a collective liquid connector collecting liquid connectors of plural analytical units to a portion,
      a collective signal connector collecting signal connectors of plural analytical units to a portion,
      a sampling means for sucking samples,
      a liquid controlling means for transferring the sucked samples and reagents, and
      a detecting means for measuring samples,
      a controller for reading out collectively contents stored in collective memory means in the plural analytical units and controlling said sampling means, said liquid controlling means, and said detecting means, and
      a signal processor for processing the observed data,
      an informing means for displaying or recording the processed results, and
      a collective connecting portion for transferring samples and reagents, and transmitting recorded contents on processing steps of the samples and processing methods of the observed data by connecting to the collective liquid connector and the collective signal connector of respective analytical units, and
   a plurality of analytical units prepared for each analytical items, wherein
   said main body of analytical apparatus
      controls flow of the samples and the reagents in plural analytical units collectively,
      accepts collectively the samples processed at respective analytical units, and
      measures their physical properties.

19. An analytical apparatus for chemical analysis comprising;
   a main body of the analytical apparatus having:
      a sampling means for sucking samples,
      a liquid controlling means for transferring the sucked samples and reagents,
      a detecting means for measuring samples, and
      a memory means storing at least an analytical method, and
   an analytical unit having:
      a liquid connector and a signal connector, both of which are to be connected to said main body of the analytical apparatus, and
      a distinguishing means corresponding to at least an analytical item, wherein
   an analytical method corresponding to said distinguishing means is selected from said memory means by connecting said analytical unit to said main body of analytical apparatus, and
   said sample is analyzed by said analytical method.

20. An apparatus for chemical analysis as claimed in claim 18, wherein said distinguishing means is a magnetic recorder storing coded signals corresponding to analytical items.

21. An apparatus for chemical analysis as claimed in claim 18, wherein said distinguishing means is a physical switch provided at a location corresponding to coded each analytical items.

22. An apparatus for chemical analysis as claimed in claim 18, wherein said distinguishing means is optical information corresponding to coded each analytical items.

* * * * *